United States Patent
Roby et al.

(10) Patent No.: US 6,936,297 B2
(45) Date of Patent: Aug. 30, 2005

(54) SILICONIZED SURGICAL NEEDLES AND METHODS FOR THEIR MANUFACTURE

(75) Inventors: Mark S. Roby, Killingworth, CT (US); John J. Kennedy, Guilford, CT (US); Nicholas Maiorino, Branford, CT (US); Alan Cabezas, Ansonia, CT (US)

(73) Assignee: Tyco Healthcare Group, LP, Norwalk, CT (US)

( * ) Notice: Subject to any disclaimer, the term of this patent is extended or adjusted under 35 U.S.C. 154(b) by 132 days.

(21) Appl. No.: 09/964,901

(22) Filed: Sep. 27, 2001

(65) Prior Publication Data

US 2003/0114882 A1 Jun. 19, 2003

(51) Int. Cl.⁷ ................................................. B05D 3/02
(52) U.S. Cl. ........................ 427/2.1; 427/2.28; 427/387; 427/421; 427/435
(58) Field of Search ............................... 427/2.1, 2.28, 427/372.2, 384, 387, 383.7, 421, 435

(56) References Cited

U.S. PATENT DOCUMENTS

| | | | |
|---|---|---|---|
| 3,574,673 A | 4/1971 | Schweiger et al. | 117/132 |
| 3,767,385 A | 10/1973 | Slaney | 75/122 |
| 3,816,920 A | 6/1974 | Sastri | 30/346.54 |
| 4,720,521 A | 1/1988 | Spielvogel et al. | 524/862 |
| 4,806,430 A | 2/1989 | Spielvoget et al. | 428/450 |
| 4,844,986 A | 7/1989 | Karakelle et al. | 428/447 |
| 5,181,416 A | 1/1993 | Evans | 73/104 |
| 5,185,006 A | 2/1993 | Williamitis et al. | 604/265 |
| 5,258,013 A | 11/1993 | Granger et al. | 606/223 |
| 5,266,359 A | 11/1993 | Spielvogel | 427/388.4 |
| 5,456,948 A * | 10/1995 | Mathisen et al. | 427/387 |
| 5,458,616 A | 10/1995 | Granger et al. | 606/223 |
| 5,533,982 A | 7/1996 | Rizk et al. | 604/239 |
| 5,534,609 A | 7/1996 | Lewis et al. | 528/15 |
| 5,536,582 A * | 7/1996 | Prasad et al. | 428/450 |
| 5,688,747 A * | 11/1997 | Khan et al. | 508/208 |
| 5,702,387 A | 12/1997 | Arts et al. | 606/45 |
| 5,736,251 A | 4/1998 | Pinchuk | 428/447 |
| 5,911,711 A * | 6/1999 | Pelkey | 604/265 |
| 5,985,355 A * | 11/1999 | Walther et al. | 427/2.28 |
| 6,015,398 A | 1/2000 | Arimatsu et al. | 604/272 |
| 6,046,143 A | 4/2000 | Khan et al. | 508/208 |
| 6,296,893 B2 * | 10/2001 | Heinz et al. | 427/2.28 |

FOREIGN PATENT DOCUMENTS

| | | | | |
|---|---|---|---|---|
| EP | 0 494 648 A2 | * | 7/1992 | ........... A61L/31/00 |
| EP | 0 627 474 A1 | | 12/1994 | |
| EP | 0 848 055 A1 | | 6/1998 | |
| EP | 878206 | * | 11/1998 | |
| JP | 06-088025 | * | 3/1994 | |

* cited by examiner

*Primary Examiner*—Erma Cameron

(57) ABSTRACT

A siliconized surgical needle is provided which requires significantly less force to effect tissue penetration than a standard siliconized needle.

17 Claims, No Drawings

SILICONIZED SURGICAL NEEDLES AND METHODS FOR THEIR MANUFACTURE

BACKGROUND

1. Technical Field

The present disclosure generally relates to siliconized surgical needles. More particularly, the present disclosure is directed to siliconized surgical needles having reduced tissue penetration force and methods for making such needles employing a coating mixture of at least one polydialkylsiloxane and at least one other siliconization material.

2. Background of Related Art

In general, the siliconization of metallic cutting edges of articles such as, for example, razor blades, hypodermic needles, scissors, scalpels, and curettes, is known. For example, Dow Corning Corporation's Dow Corning® MDX4-4159 Fluid has been used to siliconize cutting edges with an ambient temperature and humidity-curable mixture of an aminoalkyl siloxane and a cyclosiloxane dissolved in a mixture of Stoddard solvent and isopropyl alcohol.

U.S. Pat. No. 3,574,673, the contents of which are incorporated by reference herein, discloses the silicone coating of a cutting edge employing a siliconization fluid containing a mixture of copolymerizable silicones made up of an aminoalkyl siloxane, specifically a (polyaminoalkyl) alkoxysilane, and a dimethylpolysiloxane.

Other examples include U.S. Pat. Nos. 5,258,013 and 5,458,616 which disclose coating surgical needles with a siliconization material containing an aminoalkyl siloxane and a cyclosiloxane employing ultrasonic radiation. The siliconization material can be applied in a solvent carrier, e.g., hexane or heptane.

Yet another example is U.S. Pat. No. 5,985,355 which discloses coating surgical needles by (1) coating the needle with a coating solution comprising a highly condensable polydimethylsiloxane in a solvent to form a leveling coat; (2) evaporating the solvent from the first coating; (3) curing the leveling coating to polymerize the polydimethylsiloxane; (4) applying a second coating solution over the leveling coat comprising a polydimethylsiloxane having amino and alkoxy functional groups and a solvent; and (5) evaporating the solvent from the second coating.

It would be advantageous to provide siliconized surgical needles which exhibit significantly reduced penetration force upon each passage through tissue during a suturing operation.

SUMMARY

It has been discovered that a silicone coating derived from a coating mixture comprising at least one polydialkylsiloxane having a molecular weight sufficient to provide a viscosity of the coating mixture of at least about 10,000 cp and at least one other siliconization material can be applied to a surgical needle to provide a siliconized surgical needle in which the siliconized needle exhibits an average tissue penetration force below that of a standard siliconized surgical needle. In one embodiment of the present disclosure there is provided a siliconized surgical needle obtained by applying to the surface of the needle a coating mixture comprising at least one polydialkylsiloxane having a molecular weight sufficient to provide a viscosity of the coating mixture of at least about 10,000 cp and at least one other siliconization material and thereafter curing the coating mixture to provide a copolymerized coating on the needle.

In another embodiment of the present disclosure, a siliconized surgical needle can be obtained by applying to the surface of the needle a coating mixture containing a polydialkylsiloxane and at least one siliconization material which does not covalently bond with the polydialkylsiloxane and thereafter subjecting the coating mixture to curing conditions such that the siliconization material cross-links thereby interlocking the polydialkylsiloxane in the coating to provide an interpenetrating networked coating.

The expression "standard siliconized surgical needle" or "standard needle" as used herein refers to a commercially available siliconized surgical needle, e.g., the siliconized surgical needles attached to sutures marketed by Ethicon, Inc. (Somerville, N.J.).

While the amount of force required to achieve penetration of tissue during suturing may initially be about the same for the siliconized surgical needle of this disclosure and a standard siliconized surgical needle, and while both needles will tend to experience an increase in penetration force with each successive passage through tissue, at the conclusion of any given number of such passages, the siliconized needle of this disclosure will exhibit significantly less penetration force than the standard needle. Thus, the siliconized needle of this disclosure will retain its initial tissue penetration characteristics to a greater extent than a standard siliconized needle in a manner which is particularly advantageous, as it reduces the effort required in the suturing operation. This is significantly beneficial in those cases involving extensive wound closure.

DESCRIPTION OF THE PREFERRED EMBODIMENTS

Preferred embodiments of the present disclosure involve the use of coatings to produce siliconized surgical needles. It has been discovered that by coating a surgical needle with a coating mixture containing at least one polydialkylsiloxane having a molecular weight sufficient to provide a viscosity of the coating mixture of at least about 10,000 cp and at least one siliconization material, a siliconized surgical needle is provided which exhibits a significantly reduced tissue penetrating force compared with that of a standard surgical needle after an equivalent number of passages through the same, or substantially the same, tissue. Thus, the average tissue penetration force of the siliconized needle herein will advantageously be less than about 10%, preferably less than about 20% and more preferably less than about 30%, of the average tissue penetration force of a standard siliconized needle from after about 5 to about 20 passes through the same or similar tissue.

Surgical needles which can be coated with the coating mixture in accordance with this disclosure can be manufactured from a variety of metals. Such metals include, for example, Series 400 and Series 300 stainless steels. Other suitable metals for the fabrication of surgical needles include the quaternary alloys disclosed in U.S. Pat. Nos. 3,767,385 and 3,816,920, the contents of which are incorporated by reference herein. A preferred quaternary alloy possesses the ranges of components set forth below in Table I:

TABLE I

COMPOSITION OF SURGICAL NEEDLE QUATERNARY ALLOY (WT. %)

| Component(s) | Broad Range | Preferred Range | Most Preferred Range |
|---|---|---|---|
| Nickel | 10–50 | 24–45 | 30–40 |
| Cobalt | 10–50 | 25–45 | 30–40 |
| Nickel + Cobalt | 50–85 | 60–80 | 65–75 |
| Chromium | 10–30 | 12–24 | 15–22 |

TABLE I-continued

COMPOSITION OF SURGICAL NEEDLE
QUATERNARY ALLOY (WT. %)

| Component(s) | Broad Range | Preferred Range | Most Preferred Range |
|---|---|---|---|
| Molybdenum, tungsten and/or niobium (columbium) | 5–20 | 8–16 | 10–13 |

Another preferred quaternary alloy within Table I which can be utilized for the siliconized needle of this disclosure, designated MP35N, is available in wire form from Maryland Specialty Wire, Inc. (Cockeysville, Md.) and contains (nominal analysis by weight): nickel, 35%; cobalt, 35%; chromium, 20% and molybdenum, 10%.

In general, application of a coating mixture containing at least a polydialkylsiloxane having a molecular weight sufficient to provide a viscosity of the coating mixture of at least about 10,000 cp and at least one siliconization material to a surgical needle followed by curing will provide a siliconized surgical needle meeting the requirements of this disclosure.

Suitable polydialkylsiloxanes for use in forming the coating mixture herein include polydimethylsiloxanes, polydiethylsiloxanes, polydipropylsiloxanes, polydibutylsiloxanes and the like with polydimethylsiloxanes being preferred. Particularly preferred polydimethylsiloxanes are polydimethylsiloxanes having a molecular weight sufficient to provide a viscosity of the coating mixture of at least about 10,000 cp and preferably of at least about 30,000 cp. Such polydimethylsiloxanes for use herein are the products sold by Dow Coming under the name "SYL-OFF® DC 23", which is suitable as a high density condensable polydimethylsiloxane, and NuSil Technology under the name "MED 1-4162" (30,000 cp.)

Suitable siliconization materials for addition with the foregoing polydialkylsiloxanes to form the coating mixtures of this disclosure include siliconization materials containing an aminoalkyl siloxane and at least one other copolymerizable siloxane, e.g., an alkylpolysiloxane or a cyclosiloxane; a silicone oil, e.g., one sold by Dow Coming Corporation under the name Dow 360 MEDICAL FLUID (350 to 12,500 centistokes), and the like with the siliconization material containing an aminoalkyl siloxane and at least one other copolymerizable siloxane being preferred. Generally, the preferred siliconization material includes (a) from about 5 to about 70 weight percent of an aminoalkyl siloxane of the general formula

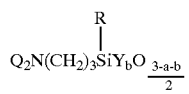

wherein R is a lower alkyl radical containing no more than about 6 carbon atoms; Y is selected from the group consisting of —OH and —OR' radicals in which R' is an alkyl radical of no more than about 3 carbon atoms; Q is selected from the group consisting of hydrogen, —$CH_3$ and —$CH_2CH_2NH_2$; a has a value of 0 or 1, b has a value of 0 or 1 and the sum of a+b has a value of 0, 1 or 2; and (b) from about 30 to about 95 weight percent of a methyl substituted siloxane of the general formula

wherein R" is selected from the group consisting of —OH and —$CR_3$ radicals and c has a value of 1 or 2. The two components of this siliconization material copolymerize, forming a lubricating coating on the surface of the needle.

In addition to, or in lieu of, the foregoing second copolymerizable siloxane, one can use one or more cyclosiloxanes such as, e.g., those described in the "Encyclopedia of Polymer Science and Engineering", Mark et al., eds., $2^{nd}$ ed., Vol.15, John Wiley & Son (1989), p. 207 et seq., the contents of which are incorporated by reference herein, provided, of course, the total amount of the second copolymerizable siloxane(s) is within the aforestated range.

A particularly preferred siliconization material for use herein in combination with the aforementioned polydimethylsiloxane(s) to form the coating mixture is Dow Corning Corporation's Dow Corning® MDX 4-4159 Fluid ("MDX Fluid"), an active solution of dimethyl cyclosiloxanes and dimethoxysilyldimethylaminoethylaminopropyl silicone polymer in a mixture of Stoddard solvent (mineral spirits) and isopropyl alcohol. Another preferred siliconization material is NuSil Technology's MED-4159.

In one embodiment of the present disclosure, the coating mixture can be formed by adding a first solution of at least one of the foregoing polydialkylsiloxanes in a solvent with a second solution of at least one of the foregoing siliconization materials in a solvent. Under preferred conditions, the first solution can be prepared by adding SYL-OFF DC 23, MED1-4162 or both in a solvent such as, for example, a hydrocarbon solvent having from about 5 to about 10 carbon atoms, e.g., pentane, hexane, heptane, octane, etc., xylene, chlorinated solvents, THF, dioxanone and the like and mixtures thereof with hexane being preferred. The first solution is typically formed from SYL-OFF DC 23 or MED 1-4162 with hexane with SYL-OFF DC 23 or MED1-4162 being present in the concentration range of from about 10 g/l to about 70 g/l and preferably from about 35 g/l to about 45 g/l.

The second solution, also under preferred conditions, can be prepared in the form of a dilute organic solution, e.g., one prepared with a solvent such as, for example, a hydrocarbon solvent possessing from about 5 to about 10 carbon atoms, e.g., pentane, hexane, heptane, octane, etc., trichlorotrifluoroethane, 1,1,1-trichloroethane, mineral spirits, alcohols, e.g., isopropyl alcohol, and the like and mixtures thereof. It is preferred to dilute MDX Fluid (or other siliconization material) with hexane and isopropyl alcohol with MDX Fluid being present in the concentration range of from about 10 g/l to about 80 g/l and preferably from about 20 g/l to about 40 g/l. In a preferred embodiment, the siliconization material is a mixture of MED1-4162 and MDX Fluid.

The mixture will ordinarily be formed by adding the first solution of the polydialkylsiloxane in solvent with the second solution of the siliconization material in solvent in a ratio ranging from about 12:1 to about 1:12, preferably from about 6:1 to about 1:6 and more preferably from about 2:1 to about 1:2. As one skilled in the art will readily appreciate, the amount of the first and second solutions necessary in forming the mixtures herein will vary depending on the volume of mixture desired.

Once the coating mixture is formed, it can then be applied to the foregoing needles employing techniques known to one skilled in the art, e.g., by dipping, wiping, spraying, total immersion, etc, with dipping and spraying being the preferred techniques. Preferably, the needles are dipped into the coating mixture for about 5 to about 60 seconds, preferably about 10 to about 45 seconds and more preferably from about 15 to 30 seconds to form a coating on the needles. After evaporation of any dilutant or solvent carrier, the siliconized coating is cured to the desired degree.

The coating can be cured by, for example, first placing the coated needle in a humid environment, e.g., a humidification chamber, and exposing the coated needle to a temperature of from about 10° C. to about 50° C. and preferably from about 20° C. to about 35° C. in a relative humidity of from about 20% to about 80% and preferably from about 50% to about 65%. The coated needles are subjected to the foregoing temperatures and humidities to initiate curing to the desired degree and provide an improved lubrication coating. Typically, a time period ranging from about 1 hour to about 6 hours and preferably from about 2 hours to about 4 hours is employed. The coated needles are then placed in, e.g., a furnace or oven, and cured by heating the needles to a temperature of from about 100° C. to about 200° C., preferably from about 110° C. to about 150° C. and more preferably from about 115° C. to about 150° C. for a time period ranging from about 2 hours to about 48 hours and preferably from about 15 hours to about 25 hours such that cross-linking of the polydialkylsiloxane and siliconization material occurs. In a particularly useful embodiment, the coated needles are heated to a temperature of 140° C. for 4 hours and a temperature of 120° C. for 20 hours.

In another embodiment of the present disclosure, the coating mixture herein is formed from at least a polydialkylsiloxane and a siliconization material which does not covalently bond with the polydialkylsiloxane. A suitable polydimethylsiloxane for use herein which does not covalently bond with the siliconization material is a product sold by NuSil Technology under the name "MED-4162". Generally, the mixture is formed by adding a first solution containing at least the polydimethylsiloxane in a solvent with the second solution discussed hereinabove. The first solution is preferably formed employing the polydimethylsiloxane MED-4162 in a solvent such as, for example, a hydrocarbon solvent having from about 5 to about 10 carbon atoms, e.g., pentane, hexane, heptane, octane, etc., xylene, and the like and mixtures thereof with hexane being preferred. It is particularly preferred to form the first solution from MED-4162 in hexane in generally the same ranges as the first solution discussed above and then adding the first solution and second solution in generally the same ratios as discussed above to form the coating mixture. Once the mixture is formed, it can then be applied to the surface of a surgical needle employing generally the same techniques and parameters as discussed above. The coating mixture is then subjected to curing conditions, e.g., the curing steps discussed above, such that the siliconization material polymerizes and cross-links thereby interlocking the polydimethylsiloxane in the coating resulting in an interpenetrating networked coating.

The following non-limiting examples are illustrative of the siliconized surgical needles and the method for their manufacture of the present disclosure.

EXAMPLE 1

The following example compares the effects of varying the surface preparation, the ratio of SYL-OFF DC 23 and MDX fluid components, the method of coating, the exposure to relative humidity, and the curing time and temperature for Cv-11 needles. Specifically, the variable factors were as follows:

A. Surface preparation—passivation or no passivation (Standard);

B. Mix ratio of DC23 to MDX4-4159—6:1 or 12:1;

C. Method of coating—spraying or dipping;

D. Relative Humidity (57%) Exposure—2 hours at 70° C. or 3 hours at 25° C.;

E. Curing—4 hours at 140° C. or 20 hours at 120° C.

Eight different trials were designed to examine the effects of varying the above-referenced conditions on needle test signatures. For each condition, 5 needles were tested by passing a needle through Porvair (Inmont Corporation), a microporous polyurethane membrane of about 0.042 inches thickness which served to simulate flesh. The amount of force in grams to achieve penetration of the Porvair by the needle was then measured for each of eight successive penetrations of the 5 needles for each trial.

Measurement of the needle penetration force was accomplished using the test procedure and apparatus described in U.S. Pat. No. 5,181,416, the contents of which are incorporated by reference herein. The test was performed by a testing fixture and an Instron Universal Testing Machine. The surgical needles were mounted in a gripping clamp which fixed the needle in a position perpendicular to the Porvair surface and oriented on its radial profile with the axis of rotation on the same plane as the plane of the Porvair. The needle was rotated into the Porvair which was mounted on top of an Instron load cell. The maximum amount of vertical force is recorded as the needle is pushed through the Porvair. The results of the variables for these tests are set forth below in Table II.

TABLE II

| | | | Factors | | |
|---|---|---|---|---|---|
| Trial | A Needle Substrate[1] | B Ratio[2] | C Application | D 57% Relative Humidity Cure | E Oven Cure |
| 1 | Passivated | 6:1 | Spray | 2 hours 70° C. | 4 hours, 140° C. |
| 2 | Standard | 12:1 | Dip | 3 hours 25° C. | 20 hours, 120° C. |
| 3 | Passivated | 12:1 | Spray | 3 hours 25° C. | 20 hours, 120° C. |
| 4 | Standard | 12:1 | Spray | 2 hours 70° C. | 4 hours, 140° C. |
| 5 | Standard | 6:1 | Spray | 3 hours 25° C. | 20 hours, 120° C. |
| 6 | Passivated | 12:1 | Dip | 2 hours 70° C. | 4 hours, 140° C. |
| 7 | Passivated | 6:1 | Dip | 3 hours 25° C. | 20 hours, 120° C. |
| 8 | Standard | 6:1 | Dip | 2 hours 70° C. | 4 hours, 140° C. |

[1]Each of the needles were coated with a mixture containing:
Syl-Off DC 23 concentration 40 g/L of solvent
Solvent used: Hexane
MDX4-4159 concentration 27 g/L of solvent
Solvent used: Hexane 85% and IPA 15%
[2]The ratio is based on Syl-Off DC 23: MDX 4-4159

The results of all 8 trials were then compared for slope of regression analysis, standard deviation of the insertion force for each of the 5 needles per trial, and the initial insertion force for each of the 5 needles. The results of the tests were reviewed to give an average ranking for initial penetration, standard deviation, and slope. The overall average rank was then compared to the variation of the factors to obtain a score for each. Table III below shows trial rankings ($1^{st}$ to $8^{th}$) for penetration, deviation, and slope, with an overall average rank.

The lower the average rank, the better.

TABLE III

| Trial # | 1 | 2 | 3 | 4 | 5 | 6 | 7 | 8 |
|---|---|---|---|---|---|---|---|---|
| Initial Penetration | 4 | 3 | 7 | 6 | 5 | 1 | 2 | 1 |
| Standard Deviation | 4 | 2 | 6 | 5 | 7 | 8 | 1 | 3 |
| Slope of regression | 7 | 1 | 8 | 4 | 3 | 2 | 5 | 6 |

TABLE III-continued

| Trial # | 1 | 2 | 3 | 4 | 5 | 6 | 7 | 8 |
|---|---|---|---|---|---|---|---|---|
| line | | | | | | | | |
| Overall average rank | 5 | 2 | 7 | 5 | 5 | 3.67 | 2.67 | 3.67 |

EXAMPLE 2

This Example compared the lubricity of needles coated with 25 mL(40 g/L) Dow SYL-OFF DC 23 with Hexane and 20 mL(27 g/L) NuSil MED-4159 with Hexane (85%) and IPA (15%) in a 2:1 ratio, with needles coated with 25 ml (40 g/L) NuSil MED 4162 with Hexane and 20 ml (27 g/L) MDX4-4159 with Hexane (85%) and IPA (15%).

Needles to be coated were placed onto a wire screen mesh (80 mesh) and submerged into the siliconization mixture for approximately 15–30 seconds. The needles were removed from the solution and then placed onto a second wire mesh and subjected to curing conditions.

Table V below outlines the various factors in curing the needles and Table VI ranks the needles in accordance with the results obtained.

TABLE V

| TRIAL | SILICONIZATION MATERIAL |
|---|---|
| 1 | Dow Syl-Off DC 23 and NuSil MED 4159 |
| 2 | NuSil MED-4162 and Dow MDX4-4159 |
| 3 | Dow Syl-Off DC 23 and Dow MDX4-4159 |
| 4 | NuSil MED-4162 and NuSil MED 4159 |

All trials were cured with humidity at 57% for 3 hours at 25° C.
All trials were cured with heat at 120° C. for 21 hours.
The solvent used was Hexane 85% & IPA 15%, by volume.
The Ratio of components was: 2:1 Syl Off &/or MED-4162 (40 g/L) to MDX4-4159 &/or MED-4159 (27 g/L)

TABLE VI

| Trial | 1 | 2 | 3 | 4 |
|---|---|---|---|---|
| Int. Pen. | 1 | 2 | 4 | 3 |
| Std Dev | 4 | 1 | 2 | 3 |
| Slope | 3 | 1 | 2 | 4 |
| Overall Rank | 2.78 | 1.3 | 2.7 | 3.3 |

EXAMPLE 3

This example tested the effects of temperature and humidity on the formation of the silicone coating. The siliconizaton material was 163 mL (40 g/L) of NuSil MED-4162 with hexane and 130 mL (27 g/L) of MDX4-4159 with hexane (85%) and IPA (15%).

An aluminum sheet was placed over a tray and a DeVilbiss Model GFG-HVLP Prime Time Gravity Feed Spray Gun was used to spray the siliconization material in a two-second burst onto the aluminum sheet. Needles were placed onto the surface of the aluminum sheet and then were sprayed in a three-second burst with the siliconizaton material.

The needles were then subjected to curing conditions at 57% relative humidity and heated for various times. Table VII below outlines the various factors for the treatments and Table VIII ranks the needles in accordance with the results obtained.

TABLE VII

| FACTORS | Humidification 1 | Oven Cure 1 | Humidification 2 | Oven Cure 2 |
|---|---|---|---|---|
| 1 | 57% RH 25° C.-3 hrs | 120° C.-2 hrs | None | 150° C.-4 hrs |
| 2 | 57% RH 25° C.-3 hrs | 150° C.-4 hrs | 57% RH 25° C.-2 hrs | 120° C.-20 hrs |
| 3 | 57% RH 25° C.-3 hrs | 150° C.-1 hr | None | 120° C.-20 hrs |
| 4 | 57% RH 25° C.-24 hrs | 150° C.-2 hrs | 57% RH 25° C.-2 hrs | 120° C.-20 hrs |
| 5 | 57% RH 25° C.-3 hrs | 150° C.-2 hrs | 57% RH 25° C.-2 hrs | 120° C.-20 hrs |
| 6 | 57% RH 25° C.-3 hrs | 140° C.-4 hrs | None | 120° C.-20 hrs |
| 7 | 57% RH 25° C.-3 hrs | 150° C.-4 hrs | None | 120° C.-12 hrs |
| 8 | 57% RH 25° C.-3 hrs | None | None | 120° C.-24 hrs |

The solvent used: Hexane 85% & IPA 15%, by volume.
The Ratio: 2:1 MED-4162 (40 g/L): TO: MDX4-4159 (27 g/L)

TABLE VIII

| Trial # | 1 | 2 | 3 | 4 | 5 | 6 | 7 | 8 |
|---|---|---|---|---|---|---|---|---|
| Int. Pen | 3 | 5 | 1 | 4 | 7 | 8 | 6 | 2 |
| Std. Dev. | 1 | 3 | 6 | 7 | 8 | 2 | 4 | 5 |
| Slope | 1 | 2 | 8 | 4 | 6 | 3 | 5 | 7 |
| Overall Avg | 1.7 | 3.3 | 5.0 | 5.0 | 7.0 | 4.3 | 5.0 | 4.7 |

It will be understood that various modifications may be made to the embodiments disclosed herein. Therefore the above description should not be construed as limiting, but merely as exemplifications of preferred embodiments. For example, metal surfaces other than needles can be coated with the coating mixture in accordance with the methods described herein. Those skilled in the art will envision other modifications within the scope and spirit of the claims appended hereto.

What is claimed is:

1. A method for manufacturing a siliconized surgical needle comprising the steps of: providing a surgical needle having a tissue penetrating end, a suture attachment end and a surface; applying a coating mixture on the surface of the needle, the coating mixture comprising an organic solvent, at least one polydialkylsiloxane having a molecular weight sufficient to provide a viscosity of the coating mixture of at least about 10,000 cp and at least one other siliconization material; and, curing the coating mixture on the surface of the needle to provide a silicone coating thereon.

2. The method of claim 1 wherein the coating mixture further comprises a first solution comprising polydimethylsiloxane and a hydrocarbon solvent selected from the group consisting of hexane and heptane and a second solution comprising a polydimethylsiloxane having amino and alkoxy functional groups and a solvent selected from the group consisting of hexane, heptane, isopropanol and mixtures thereof.

3. The method of claim 2 wherein the step of curing the coating mixture comprises: subjecting the coating mixture to an atmosphere of from about 20% to about 80% relative humidity, at a temperature from about 10° C. to about 50° C. for a time period ranging from about 1 hour to about 6 hours; and, heating the coating mixture to a temperature of from about 100° C. to about 200° C. for a time period ranging from about 2 hours to about 48 hours to effectively polymerize the polydimethylsiloxane and polydimethylsiloxane having amino and alkoxy functional groups.

4. The method of claim 2 wherein the step of curing the coating mixture comprises: subjecting the coating mixture to an atmosphere of from about 50% to about 65% relative humidity, at a temperature from about 20° C. to about 35° C. for a time period ranging from about 2 hours to about 4 hours; and, heating the coating mixture to a temperature of from about 115° C. to about 150° C. for a time period ranging from about 15 hours to about 25 hours to effectively polymerize the polydimethylsiloxane and polydimethylsiloxane having amino and alkoxy functional groups.

5. The method of claim 4 wherein the coating mixture is heated to a temperature of 140° C. for 4 hours and then heated to a temperature of 120° C. for 20 hours.

6. The method of claim 2 wherein the ratio of the first solution to the second solution is from about 1:6 to about 6:1.

7. The method of claim 1 wherein the step of applying the coating mixture on the surface of the needle is selected from the group consisting of dipping, spraying or wiping.

8. The method of claim 1 wherein the step of curing the coating mixture comprises: subjecting the coating mixture to an atmosphere of from about 20% to about 80% relative humidity, at a temperature from about 10° C. to about 50° C. for a time period ranging from about 1 hour to about 6 hours; and, heating the coating mixture to a temperature of from about 100° C. to about 200° C. for a time period ranging from about 2 hours to about 48 hours to effectively polymerize the polydialkylsiloxane and siliconization material.

9. The method of claim 1 wherein the step of curing the coating mixture comprises: subjecting the coating mixture to an atmosphere of from about 50% to about 65% relative humidity, at a temperature from about 20° C. to about 35° C. for a time period ranging from about 2 hours to about 4 hours; and, heating the coating mixture to a temperature of from about 115° C. to about 150° C. for a time period ranging from about 15 hours to about 25 hours to effectively polymerize the polydialkylsiloxane and siliconization material.

10. The method of claim 1 wherein the coating mixture further comprises a first solution comprising the polydialkylsiloxane and a first organic solvent and a second solution comprising the siliconization material and a second organic solvent.

11. The method of claim 10 wherein the first solution comprises polydimethylsiloxane and the first solvent is at least one hydrocarbon solvent of from about 5 to about 10 carbon atoms.

12. The method of claim 10 wherein the first solution comprises polydimethylsiloxane and hexane.

13. The method of claim 10 wherein in the second solution the siliconization material comprises an aminoalkyl siloxane and at least one other siloxane copolymerizable therewith and the solvent is at least one of a hydrocarbon solvent of from about 5 to about 10 carbon atoms and an alcohol.

14. The method of claim 13 wherein in the second solution the siliconization material comprises a polydimethylsiloxane having amino and alkoxy functional groups and the solvent is selected from the group consisting of hexane, heptane, isopropanol and mixtures thereof.

15. The method of claim 10 wherein in the second solution the siliconization material comprises a polydimethylsiloxane having amino and alkoxy functional groups and the solvent is at least one of a hydrocarbon solvent of from about 5 to about 10 carbon atoms and an alcohol.

16. A method as in claim 10 wherein the first organic solvent is the same as the second organic solvent.

17. A method for manufacturing a siliconized surgical needle comprising the steps of: providing a surgical needle having a tissue penetrating end, a suture attachment end and a surface; applying a single coating mixture on the surface of the needle, the single coating mixture comprising an organic solvent, at least one polydialkylsiloxane having a molecular weight sufficient to provide a viscosity of the coating mixture of at least about 10,000 cp and at least one other siliconization material; and, curing the single coating mixture on the surface of the needle to provide a silicone coating thereon.

* * * * *